(12) United States Patent
Seitz (10) Patent No.: US 7,659,991 B2
(45) Date of Patent: Feb. 9, 2010

(54) COLORIMETRIC THREE-DIMENSIONAL MICROSCOPY

(75) Inventor: Peter Seitz, Urdorf (CH)

(73) Assignee: Heliotis AG, Zurich (CH)

( * ) Notice: Subject to any disclaimer, the term of this patent is extended or adjusted under 35 U.S.C. 154(b) by 188 days.

(21) Appl. No.: 11/894,960

(22) Filed: Aug. 22, 2007

(65) Prior Publication Data

US 2008/0049234 A1      Feb. 28, 2008

Related U.S. Application Data

(60) Provisional application No. 60/839,424, filed on Aug. 23, 2006.

(51) Int. Cl.
*G01B 11/02* (2006.01)
(52) U.S. Cl. ..................................... 356/497
(58) Field of Classification Search ................ 356/477, 356/479, 497; 250/227.19, 227.27; 385/12
See application file for complete search history.

(56) References Cited

U.S. PATENT DOCUMENTS

| | | | |
|---|---|---|---|
| 3,013,467 A | | 12/1961 | Minsky |
| 5,459,570 A | | 10/1995 | Swanson et al. |
| 5,640,270 A | | 6/1997 | Aziz et al. |
| 5,929,999 A | * | 7/1999 | Butterworth ................ 356/405 |
| 6,134,003 A | * | 10/2000 | Tearney et al. ............. 356/479 |
| 6,191,862 B1 | * | 2/2001 | Swanson et al. ............ 356/479 |
| 6,501,551 B1 | * | 12/2002 | Tearney et al. ............. 356/477 |
| 7,336,366 B2 | * | 2/2008 | Choma et al. ............... 356/479 |
| 7,468,997 B2 | * | 12/2008 | Jayaraman ................... 372/20 |

(Continued)

FOREIGN PATENT DOCUMENTS

EP      1 458 087 A1      9/2004

(Continued)

OTHER PUBLICATIONS

Leitgeb, R.:"Performance of fourier domain vs. time domain optical coherence tomography," Optics Express, Apr. 21, 2003, pp. 889-894, vol. 11, No. 8, Optical Society of America, US.

(Continued)

*Primary Examiner*—Michael A Lyons
(74) *Attorney, Agent, or Firm*—Weingarten, Schurgin, Gagnebin & Lebovici LLP (57) ABSTRACT

An optically reflective or translucent object (14) can be microscopically imaged in all three dimensions and in true color for observation by a human observer. An interferometric optical setup is employed, using the low temporal coherence of a tunable broad-band light source (10, 20) to resolve the axial dimension, a single opto-mechanical or electronic scanning mechanism for accessing different object depths, and a two-dimensional photo sensor device (15, 34) capable of demodulating the temporally or spatially modulated scanning signals to reconstruct the object's full volume. Three volume scans are carried out sequentially, and the tunable broad-band source (10, 20) is operated in such a way that its spectral distribution for each of the volume scans results in an effective system sensitivity corresponding to one of the three CIE (Commission Internationale d'Éclairage) tristimulus curves, or a linear combination thereof. The linear combination of the three volume images forms the full, true-color volume image for human observers. By using reference objects (43) in the imaged volume, the three-dimensional images can be corrected for spatially- and wavelength-dependent dispersion and absorption.

22 Claims, 3 Drawing Sheets

U.S. PATENT DOCUMENTS

| | | |
|---|---|---|
| 2003/0043381 A1 | 3/2003 | Fercher |
| 2005/0185192 A1 | 8/2005 | Kim et al. |

FOREIGN PATENT DOCUMENTS

| | | |
|---|---|---|
| WO | WO 02/088705 | 11/2002 |
| WO | WO2005/001401 | 1/2005 |
| WO | WO2005/047813 | 5/2005 |

OTHER PUBLICATIONS

Wiesauer, K., et al: "Ultra-high resolution optical coherence tomography for material characterization and quality control," Proceedings of SPIE, 2005, pp. 108-115, vol. 5714, SPIE, Bellingham, WA, US.

Lingfeng Vu, et al: "Full-color three-dimensional microscopy by wide-field optical coherence tomography," Optics Express, Dec. 27, 2004, pp. 6632-6641, vol. 12, No. 26, Optical Society of America, US.

Pattern Recognition Second Edition; Sergios Theodoridis—University of Athens, Greece and Konstantinos Koutroumbas—National Observatory of Athens, Greece; Academic Press—Elsevier Science 2003.

* cited by examiner

COLORIMETRIC THREE-DIMENSIONAL MICROSCOPY

This application claims priority to U.S. provisional application No. 60/839,424 filed August 23, 2006.

TECHNICAL FIELD

The present invention relates to a calorimetric optical coherence tomography microscopy apparatus for recording three-dimensional images of an optically translucent or reflective sample object, comprising a broadband light source, and an interferometric setup for detecting three-dimensional images of an optically translucent or reflective object.

STATE OF THE ART

Standard optical microscopy provides for the imaging of three-dimensional objects with a lateral resolution of the order of a micrometer, and over the complete visual range of wavelengths. The obtained images, however, are only two-dimensional, and provide only little information about the third dimension, through the use of the very limited depth of focus.

U.S. Pat. No. 3,013,467 describes a possibility to overcome this limitation of two-dimensional images. The so-called confocal microscopy makes it possible to acquire three-dimensional microscopic images of three-dimensional objects. However, the image formation in confocal microscopy is only possible using monochromatic light, since laser light sources are required for the optical setup. In addition, the three-dimensional image acquisition in confocal microscopy necessitates three-dimensional mechanical scanning of the complete volume taken up by the object. For that reason, it is not practical to acquire three-dimensional true-color microscopic images of arbitrary objects with the techniques of confocal microscopy.

Conventional optical microscopy as well as confocal microscopy do not yield geometrically well-resolved images of objects when substantial optical scattering occurs in the volume under study. This problem can be overcome by the technique of optical coherence tomography (OCT), described in U.S. Pat. No. 5,459,570. A interferometric setup is employed for the optical measurement of the axial distribution of the local backscattering coefficient. The axial resolution of OCT microscopy is related to the spectral width of the used light, and for this reason, light sources with a spectral bandwidth that is as large as possible are being employed, as described for example by K. Wiesauer et al., "Ultra-high resolution optical coherence tomography for material characterization and quality control", Proceedings of the SPIE, Vol. 5714, pp. 108-115, 2005.

The interferometric setup of all known OCT techniques requires scanning of the axial depth coordinate, for which several different types of mechanisms have been proposed: Mechanical scanning as in time-domain OCT (TD-OCT), electronic scanning of the light source's wavelength as in time-encoded or swept-source frequency domain OCT (FD-OCT), or electronic scanning in the detector plane in spatially encoded frequency domain FD-OCT. All these techniques have in common that the data in the lateral dimensions of the objects must be acquired with a two-dimensional opto-mechanical scanning. This limitation is overcome by the technique of parallel OCT, as described for example in EP 1458087. That approach consists of acquiring and preprocessing the optical interferometric signal in each pixel simultaneously. In this way no opto-mechanical scanning in the lateral direction is required any more, and only axial depth scanning with one of the known techniques is necessary, making it possible to realize OCT microscopes capable of real-time (frame rate of 10 Hz or more) three-dimensional data acquisition. Nevertheless, the obtained volumetric OCT imagery from this and all other known OCT techniques represents luminance-only information, since it has been obtained with a single broad-band light source.

This restriction has been overcome by the use of three LEDs with central wavelengths in the blue, in the green and in the red spectral range, which are sequentially moved into place in a conventional OCT setup; this is described by L. Yu et al. in "Full-color three-dimensional microscopy by wide-field optical coherence tomography", Optics Express, Vol. 12, 27 December 2004. By mechanically scanning through the object in all three dimensions (axial and lateral), and by carrying out each of these scans for one of the three central wavelengths, a volumetric OCT data set is produced, which is perceived by human observers as partially resembling the true-color images seen with conventional optical microscopy. However, for true-color perception, the effective system sensitivity should correspond to one of the three CIE (Commission Internationale d'Éclairage) tristimulus curves or a linear combination thereof, which is generally not the case with commercially available LEDs.

Figure 1:
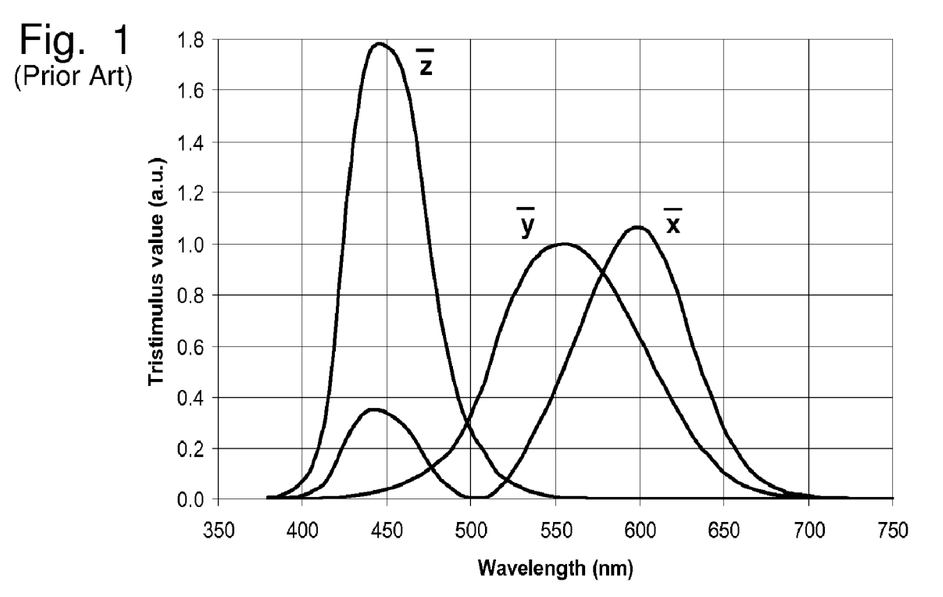
FIG. 1 shows the three tristimulus curves for the standard observer according to the CIE (*Commission Internationale de d'Eclairage*, 1931). The overall spectral sensitivity of an optical system making use of three different light sources with spectra $S_1$, $S_2$ and $S_3$ must correspond to the three curves $\bar{x}$, $\bar{y}$ and $\bar{z}$ or to a linear combination thereof, if true color acquisition for a human observer is desired.
Figure 2:
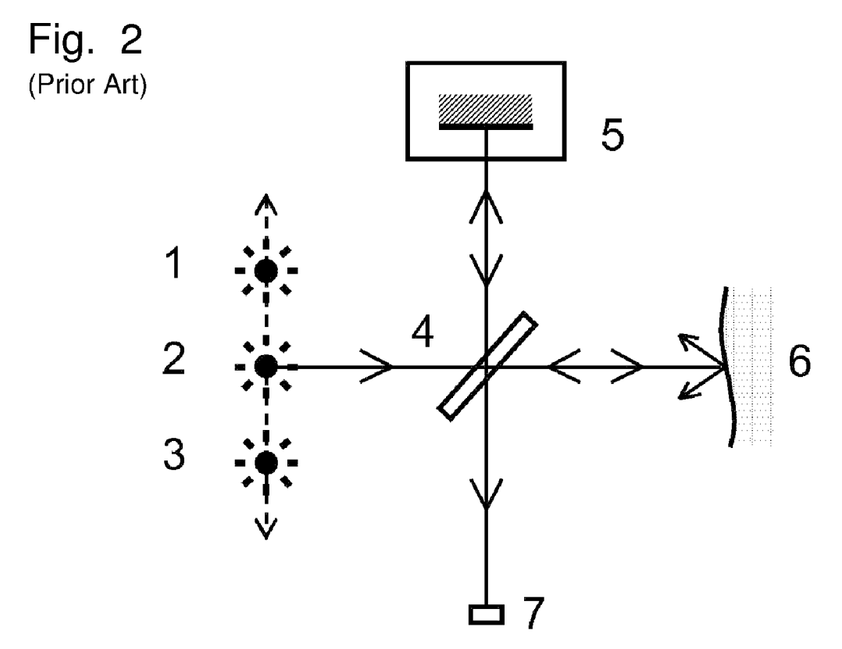
FIG. 2 schematically shows three-dimensional optical coherence tomography with three-color data acquisition according to the prior art FIG. 3 schematically shows three-dimensional optical coherence tomography with true-color data acquisition according to the present invention. The tunable light source 10 is operated sequentially in such a manner that the produced spectra $S_1$, $S_2$ and $S_3$ result in a total spectral system response corresponding to the three CIE tristimulus curves $\bar{x}$, $\bar{y}$ and $\bar{z}$ or to a linear combination thereof.

The CIE 1931 tristimulus curves (CIE Standard Colorimetric Observers CIE Standard S 014-1/E:2006, published by CIE Central Bureau, Kegelgasse 27, Vienna, Austria) are given in Table 1 and shown in FIG. 1. Referring to FIG. 2, the optical setup for a color OCT system according to prior art consists of the following elements: Broad-band light sources 1, 2, 3 are mechanically moved into place, one after the other, and used as the illumination source of an OCT interferometer. Such an interferometer consists of a beam splitter 4, partitioning the incoming light beam into a reference beam, reflected by the moving reference mirror 5, and an object beam reflected by the sample 6. The beam splitter 4 recombines the light from the two beams, and the interference pattern is sensed with the point photo detector 7. The technical realization of this color OCT setup calls for at least four axes of motion, making the resulting system technically complex and costly: The light sources and the reference mirror both must be moved along an axis, and the sample must be moved in the two lateral directions, for the acquisition of a complete volumetric color OCT data set.

All known optical microscopy techniques, conventional methods as well as methods based on OCT, suffer from the deficiency that they cannot adequately cope with the problem of optical absorption, in particular if the absorption properties of the object are dependent on the spectral wavelength, or the three-dimensional position. If an object of interest lies in a volume with a certain wavelength-dependent absorption characteristic (i.e. a certain color), then it is not possible to recover neither the absolute value of the reflection coefficient nor the color of the object itself. The reason for this is that two key pieces of information are missing: What is the total absorption length of the optically absorbing material, and what are the spectral properties of the absorbing material.

SUMMARY OF THE INVENTION

The present invention addresses the problem of the technical complexity of color OCT microscopy according to prior art, and its failure to acquire true-color OCT volumetric images that are perceived by human observers as accurately representing the actual color distribution in the object under study. In addition, the present invention also addresses the problem of optical absorption in the object under study, which may be depth- as well as wavelength-dependent.

A principle object of the invention is to provide an optical microscopy technique, capable of acquiring three-dimensional images in their full color as perceived by a human observer, and methods for the realization of easy-to-realize colorimetric three-dimensional microscopy effectively handling absorption and dispersion in the volume under study. Another object of the invention is to provide a colorimetric three-dimensional microscopy technique that can be implemented with readily available optoelectronic components, and in such a way that the complete three-dimensional acquisition process can be carried out in fractions of a second or even at video rate (25 to 30 full-color volume images per second). A further object of the invention is to provide a calorimetric three-dimensional microscopy technique that can accommodate the presence of locally varying regions of spectrally dependent absorbance or dispersion.

These and other problems are solved by the microscopy apparatus according to the present invention, and the methods according to the present invention as defined in the independent claims. Advantageous embodiments and variants are given in the dependent claims.

To solve the above-mentioned problems, an interferometric optical setup is employed, using the low temporal coherence of a tunable broad-band light source to resolve the axial dimension, a single opto-mechanical or electronic scanning mechanism for accessing different object depths, and a two-dimensional photo sensor device, capable of demodulating the temporally or spatially modulated scanning signals to reconstruct the object's full volume. Three volume scans are carried out sequentially, and the tunable broad-band source is operated in such a way that its spectral distribution for each of the volume scans results in an effective system sensitivity corresponding to one of the three CIE (Commission Internationale d'Éclairage) tristimulus curves, or a linear combination thereof. The linear combination of the three volume images then forms the full, true-color volume image for human observers. By using reference objects in the imaged volume, the three-dimensional images can be corrected for spatially- and wavelength-dependent dispersion and absorption effects.

It is also measure to obtain more than three volume scans, as long as they can be linearly combined to result in an effective system sensitivity corresponding to the three CIE (Commission Internationale d'Éclairage) tristimulus curves.

WAYS TO IMPLEMENT THE INVENTION

Figure 3:
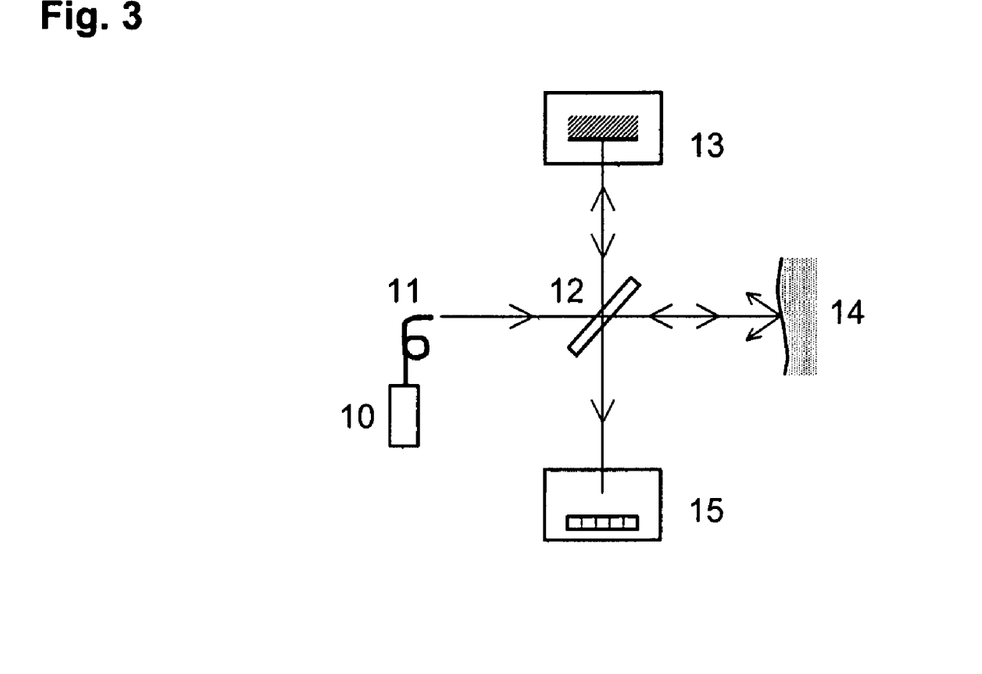

The colorimetric three-dimensional microscopy system according to the invention is schematically illustrated in FIG. 3: A tunable light source 10 is used whose emission properties can be electronically controlled to produce different emission spectra $S_1$, $S_2$ and $S_3$. The tunable light source must be able to produce light in the complete visual wavelength range (approx. 400-700 nm). The total effective spectral system response of each of said three emission spectra corresponds to one of the three CIE tristimulus curves shown in FIG. 1 (or a linear combination thereof. Since all optical elements of the OCT system with their spectral properties contribute to the total spectral system response (quantum efficiency of the photodetector, absorption characteristics of the beam path, reflection properties of beam splitter and reference mirror, emission spectrum of the light source), the emission spectrum of the tunable light source 10 must be selected and optimized accordingly.

A first possible embodiment of such a tunable light source 10 consists of an intense broad-band light source, which is filtered with an electrically or mechanically switchable filter with the above described spectral characteristics. Possible embodiments of such light sources include a high-intensity white LED, or a high-pressure gas discharge lamp with a sufficiently wide spectrum to cover all visible wavelengths (e.g. metal halide lamps).

Another possible embodiment of a tunable light source is a monochromatic light source such as a Ti:Sapphire laser system, whose wavelength and intensity are swept at high speed over the desired range, so that an averaged, effective spectrum as described above is obtained. The speed of this sweep must be so high that the detector sees a complete spectrum during the time of one fringe period of the OCT signal.

The light from the light source 10 is coupled into the multi-mode optical fiber 11, and is guided to the input of an optical interferometer, such as a Michelson, a Mach-Zehnder, or a Kösters interferometer. The interferometer type used for illustrative purposes in FIG. 3 is a Michelson interferometer, consisting of a beam splitter 12, a reference beam path with plane reference mirror 13, an object beam path with the object sample 14, and a two-dimensional image sensor 15, capable of demodulating the OCT signals produced by moving the reference mirror 13 along the reference beam path axis. A complete volumetric OCT data set for one selection of light source can therefore be acquired with one scan of the single opto-mechanical scanner that is moving the reference mirror 13. After each scan, the spectrum of the tunable light source is changed, selecting in sequence the three spectral distributions with which the effective spectral system responses that correspond to the CIE tristimulus curves are obtained.

An alternative, non-mechanical depth-scanning mechanism consists of using a fixed relative position of reference mirror and object, and by realizing the depth scanning through a dispersive optical element and electronic scanning of a one- or two-dimensional image sensor in the photodetector device, as known from FD-OCT, and as described for example by R. A. Leitgeb et al. in "Performance of Fourier domain vs. time domain optical coherence tomography," Optics Express, vol. 11, pp. 889-894, March 2003.

If the axial extent of an object under study is larger than a few ten micrometer, it becomes necessary to adapt the focus of the imaging lens (not shown) used in the OCT setup illustrated in FIG. 3 for imaging one plane of the object 14 onto the plane of the image sensor 15. In the prior art this is achieved by moving the object imaging lens synchronously with reference mirror 13. In a system according to this invention, a true-color, high-speed OCT imaging system with a single opto-mechanical scanner can be realized, as it is schematically described in FIG. 4.

Figure 4:
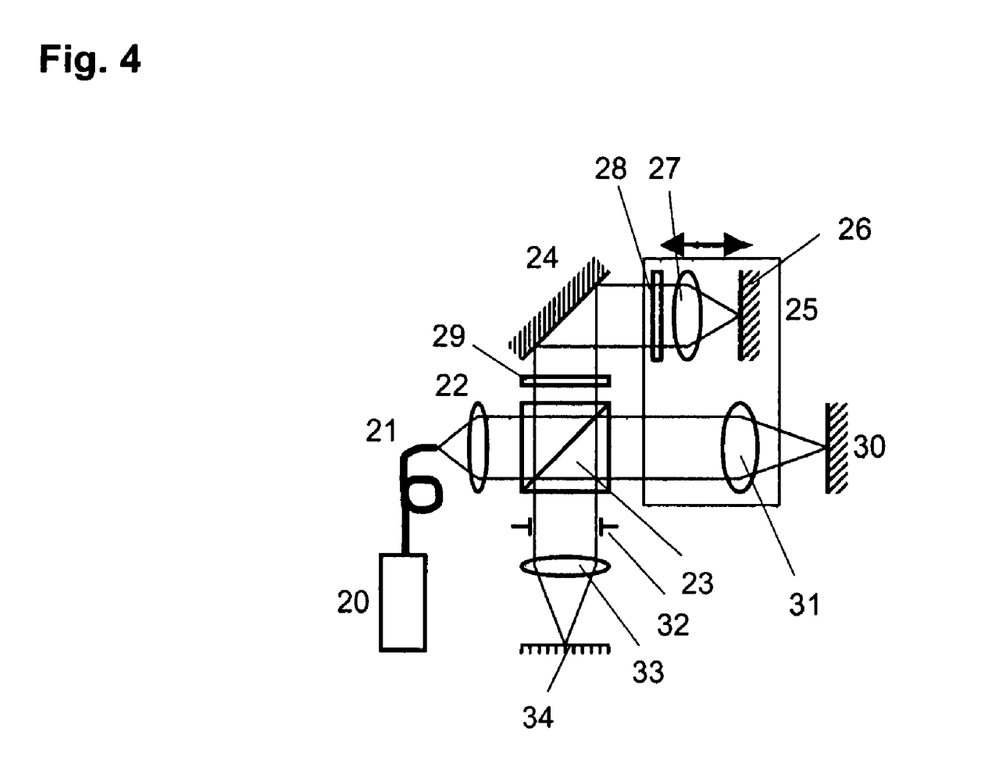
FIG. 4 schematically shows a three-dimensional optical coherence tomography apparatus with true-color data acquisition according to the present invention, offering dynamic coherent focus for the high-resolution imaging of objects with an extended depth. Only one opto-mechanical scanning element is required, moving the optical subsystem 25 with the plane reference mirror 26 and the imaging optics 31. As in FIG. 3, a tunable light source 20 is employed, with which a total system response according to the CIE tristimulus curves is achieved.

A tunable light source 20 is used, whose emission properties can be electrically controlled, in order to produce three emission spectra $S_1$, $S_2$ and $S_3$. The total spectral system response with these three emission spectra correspond to the three CIE tristimulus curves shown in FIG. 1. The light from the light source 20 is coupled into a multi-mode optical fiber 21, and the collimating lens 22 converts the emitted light into a parallel beam illuminating an optical interferometer, such as a Michelson interferometer, a Mach-Zehnder interferometer, or a Kösters interferometer. The interferometer type used for illustrative purposes in FIG. 4 is a Michelson interferometer, consisting of a beam splitter 23, partitioning the impinging source light beam into a reference beam path, and into an object beam path. The object beam path contains an object imaging lens 31, focusing the incoming light onto a focal plane 30 on or in the object under study, and collecting the reflected or scattered light from the object plane 30 back into the object beam path. In the reference beam path, a plane deflection mirror 24 redirects the light beam in such a way that it is parallel to the light in the object beam path. The light in the reference beam path is then focused by reference imaging lens 27 onto a plane reference mirror 26. The reference mirror 26 and the reference imaging lens 27, as well as the object imaging lens 31 in the object beam path are mounted on the same optical subsystem module 25, which can be moved axially by a single opto-mechanical scanner, as indicated by the double arrow. The distance from the beam splitter 24 to the reference mirror 26 is equal to the distance from the beam splitter 24 to the object focus plane 30. If the object imaging lens 31 is identical to the reference imaging lens 27, the geometrical displacement of the measurement focus in the object beam path is equal to the change in optical length in the reference beam path, thus giving the OCT apparatus dynamic coherent focus over the full scanning distance with a single opto-mechanical scanner.

It is also possible to use different lenses 27 and 31, while still obtaining dynamic coherent focus, by placing a compensation plate 28 in the reference beam path on the optical subsystem module 25. The properties of this compensation plate are chosen such that it provides for identical thicknesses and refractive properties in the reference as well as in the object beam path.

The beam splitter 23 recombines the reflected light from the reference beam path and the object beam path to a detection beam path, where the interfering light is focused with an detector imaging lens 33 onto the plane of a image sensor 34. As described above, the OCT image sensor 34 is capable of demodulating separately for each pixel the incident light, which is temporally modulated according to the axial movement of the optical subsystem module 25.

The average size of the speckles in the image sensor plane 34 varies as a function of the optical aperture 32 in the detection beam path. For optimum contrast, the average speckle size should be in the range of the effective photosensitive area of the single detector pixels. As a consequence, the aperture 32 should be chosen such that the average speckle size has optimum size. Since all components determining the optical magnification of the OCT microscope are contained in the optical subsystem module 25, a different value of the optical magnification can be realized by simply replacing one module 25 for another module 25, having a different set of lenses 31 and 27. All other parts of the OCT microscope according to the present invention are not affected.

If the object under study reflects or scatters only a small amount of light back into the interferometer, the light from the reference beam path should be correspondingly reduced, in order to improve the contrast of the detected signal in the sensor plane 34. A neutral density plate 29 arranged in the reference beam path can achieve this. The transmission ratio of said neutral density plate 29 must be chosen in way that results in optimum signal contrast for different types of objects.

Figure 5:
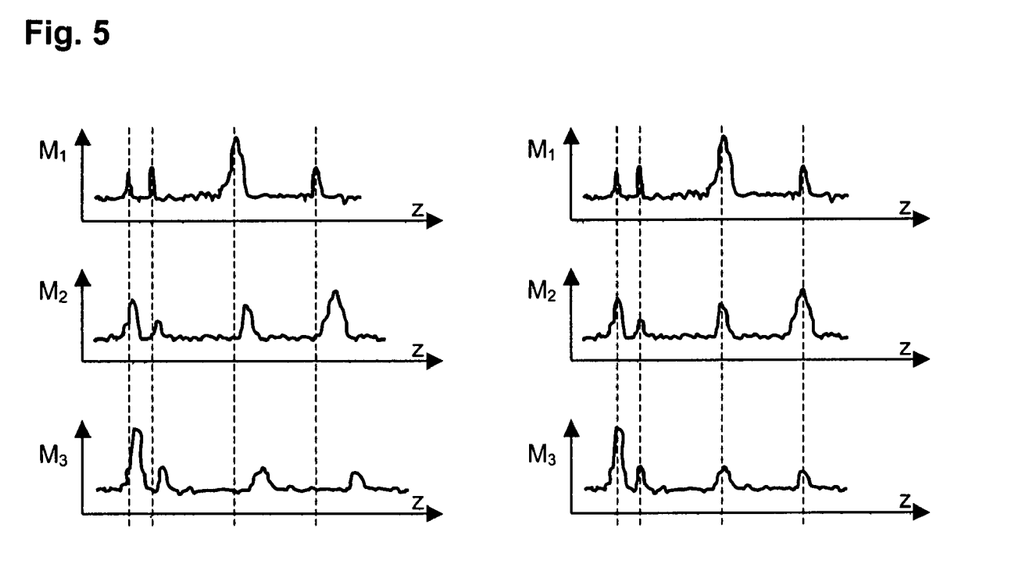
FIG. 5 shows an example of the signals $M_1$, $M_2$ and $M_3$ in one pixel acquired with the three illumination spectra $S_1$, $S_2$ and $S_3$. If the propagation speed of the light emitted by the three light sources differs in the measurement volume ("dispersion"), the depth scale of the three signals will not coincide. By making use of some reference objects, the three depth scales can be recalibrated to match up again.

If the average propagation speed of the light in the object volume under study is differing significantly for the three spectral distributions $S_1$, $S_2$ and $S_3$ of the tunable light source, i.e. if the refractive index $n(\lambda)$ shows significant variation as a function of the wavelength $\lambda$, the effect of optical dispersion will become manifest: The three depth scans measured with the three illumination spectra $S_1$, $S_2$ and $S_3$ will exhibit a different depth scale. This is illustrated in the left part of FIG. 5, showing experimental depth measurement data $M_1$, $M_2$ and $M_3$ for a single lateral position, corresponding to the three sequential depth scans with illumination spectra $S_1$, $S_2$ and $S_3$. Applying known pattern recognition techniques, as described for example by S. Theodoridis et al., "Pattern Recognition", Academic Press 2003, San Diego, chapters 7 (Feature Generation II) and 8 (Template Matching), pp. 269-349, salient signal features that correspond to the same scattering or reflecting element of the object are identified in the three measurements $M_1$, $M_2$ and $M_3$. In the simplest case, where the refractive index is changing abruptly from a first value to a second one (step function), the resulting signal feature in the three measurements will consist of the envelope of the autocorrelation function of the corresponding spectral distribution of the tunable light source. Since that function is precisely known, occurrences of it in the measured signals can be determined reliably.

Once the corresponding salient signal features in three measurements $M_1$, $M_2$ and $M_3$ have been determined, the different coordinate segments of the depth axis z of the three data sets are adapted to each other, so that the salient signal features in the three measurements coincide, as indicated on the right side of FIG. 5. The simplest method to carry out this step consists of the following technique: The first measurement $M_1$ is employed as the reference data set. For each of the two other measurements $M_2$ and $M_3$, the different coordinate sections of the depth axis, i.e. the segments between salient points, are stretched or compressed linearly, so as to let the salient signal points of the two measurements $M_2$ and $M_3$ with the distorted depth axis coincide with the salient signal points of the reference measurements $M_1$. In this way an identical depth scan axis for the three measurements can be established, effectively correcting the effect of optical dispersion.

Figure 6:
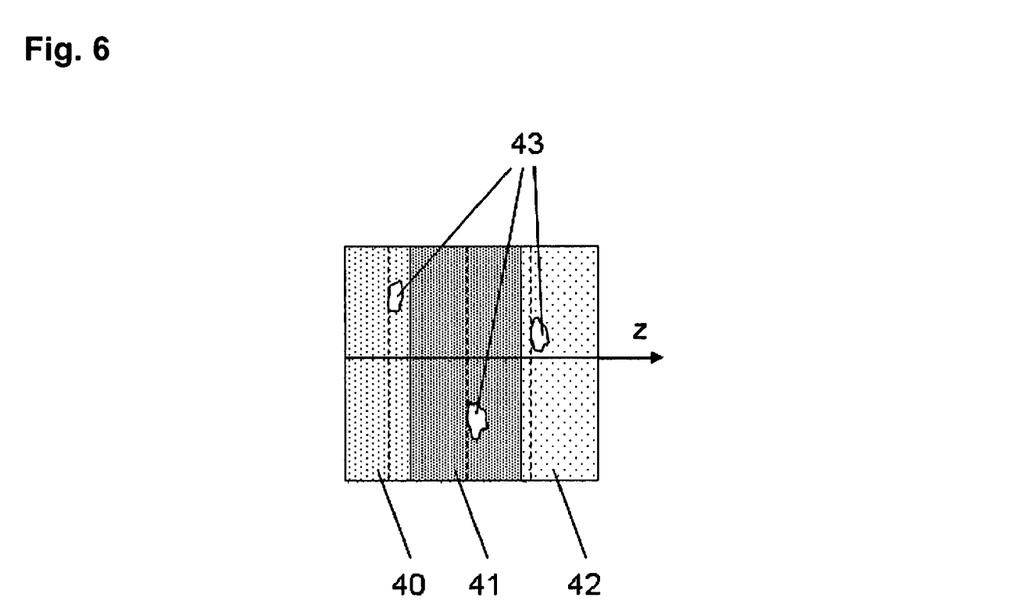
FIG. 6 shows a measurement volume with regions of differing absorption and the presence of a few objects with known spectral reflection properties as a function of depth coordinate z.

A further problem of prior art optical microscopy can be successfully addressed by a microscopy system according to the invention: In the presence of absorbing layers whose characteristics depend on the wavelength and the depth coordinate, it has not been possible until today to obtain a true-color volumetric representation of a microscopic scene. This problem is illustrated in FIG. 6, showing a structure of light absorbing layers 40, 41 and 42 with uniform absorption characteristics, as well as a few reference objects 43 with known spectral reflectance performance: Their absolute optical reflectance factors $R_1$, $R_2$ and $R_3$ for the three illumination spectra $S_1$, $S_2$ and $S_3$ of the tunable light source are known. The light arriving at the depth plane in which these objects lie (shown as dashed line in the figure) has been filtered by the multitude of layers on top of the particular object. Thus an unknown amount of the light has been absorbed. The light is reflected by the object, and is transmitted again through the same layers with their unknown absorption characteristics. Since the emitted light power $P_1$, $P_2$ and $P_3$ is known for each of the illumination spectra $S_1$, $S_2$ and $S_3$ of the tunable light source, the actually measured signal $M_i = P_i \cdot R_i \cdot A_i$ (i=1 ... 3) can be used to calculate the total attenuation coefficients $A_1$, $A_2$ and $A_3$ for the depth plane in which the known reference objects are located, by the formula $A_i = M_i/(P_i \cdot R_i)$, (i=1 ... 3). With the assumption that the object consists of homogeneous layers with constant properties in the lateral direction, it becomes possible to correct the color measurement data in the whole measurement volume, and this correction is colorimetrically accurate in all planes in which reference objects are located.

TABLE 1

Tristimulus curves x, y, z

| Wavelength [nm] | x [a.u.] | y [a.u.] | z [a.u.] |
|---|---|---|---|
| 380 | 0.001 | 0.000 | 0.007 |
| 385 | 0.002 | 0.000 | 0.011 |
| 390 | 0.004 | 0.000 | 0.020 |
| 395 | 0.008 | 0.000 | 0.036 |
| 400 | 0.014 | 0.000 | 0.068 |
| 405 | 0.023 | 0.001 | 0.110 |
| 410 | 0.044 | 0.001 | 0.207 |
| 415 | 0.078 | 0.002 | 0.371 |
| 420 | 0.134 | 0.004 | 0.646 |
| 425 | 0.215 | 0.007 | 1.039 |
| 430 | 0.284 | 0.012 | 1.386 |
| 435 | 0.329 | 0.017 | 1.623 |
| 440 | 0.348 | 0.023 | 1.747 |
| 445 | 0.348 | 0.030 | 1.783 |
| 450 | 0.336 | 0.038 | 1.772 |
| 455 | 0.319 | 0.048 | 1.744 |
| 460 | 0.291 | 0.060 | 1.669 |
| 465 | 0.251 | 0.074 | 1.528 |
| 470 | 0.195 | 0.091 | 1.288 |
| 475 | 0.142 | 0.113 | 1.042 |
| 480 | 0.096 | 0.139 | 0.813 |
| 485 | 0.058 | 0.169 | 0.616 |
| 490 | 0.032 | 0.208 | 0.465 |
| 495 | 0.015 | 0.259 | 0.353 |
| 500 | 0.005 | 0.323 | 0.272 |
| 505 | 0.002 | 0.407 | 0.212 |
| 510 | 0.009 | 0.503 | 0.158 |
| 515 | 0.029 | 0.608 | 0.112 |
| 520 | 0.063 | 0.710 | 0.078 |
| 525 | 0.110 | 0.793 | 0.057 |
| 530 | 0.166 | 0.862 | 0.042 |
| 535 | 0.226 | 0.915 | 0.030 |
| 540 | 0.290 | 0.954 | 0.020 |
| 545 | 0.360 | 0.980 | 0.013 |
| 550 | 0.433 | 0.995 | 0.009 |
| 555 | 0.512 | 1.000 | 0.006 |
| 560 | 0.595 | 0.995 | 0.004 |
| 565 | 0.678 | 0.979 | 0.003 |
| 570 | 0.762 | 0.952 | 0.002 |
| 575 | 0.843 | 0.915 | 0.002 |
| 580 | 0.916 | 0.870 | 0.002 |
| 585 | 0.979 | 0.816 | 0.001 |
| 590 | 1.026 | 0.757 | 0.001 |
| 595 | 1.057 | 0.695 | 0.001 |
| 600 | 1.062 | 0.631 | 0.001 |
| 605 | 1.046 | 0.567 | 0.001 |
| 610 | 1.003 | 0.503 | 0.000 |
| 615 | 0.938 | 0.441 | 0.000 |
| 620 | 0.854 | 0.381 | 0.000 |
| 625 | 0.751 | 0.321 | 0.000 |
| 630 | 0.642 | 0.265 | 0.000 |
| 635 | 0.542 | 0.217 | 0.000 |
| 640 | 0.448 | 0.175 | 0.000 |
| 645 | 0.361 | 0.138 | 0.000 |
| 650 | 0.284 | 0.107 | 0.000 |
| 655 | 0.219 | 0.082 | 0.000 |
| 660 | 0.165 | 0.061 | 0.000 |
| 665 | 0.121 | 0.045 | 0.000 |
| 670 | 0.087 | 0.032 | 0.000 |
| 675 | 0.064 | 0.023 | 0.000 |
| 680 | 0.047 | 0.017 | 0.000 |
| 685 | 0.033 | 0.012 | 0.000 |
| 690 | 0.023 | 0.008 | 0.000 |
| 695 | 0.016 | 0.006 | 0.000 |
| 700 | 0.011 | 0.004 | 0.000 |
| 705 | 0.008 | 0.003 | 0.000 |
| 710 | 0.006 | 0.002 | 0.000 |
| 715 | 0.004 | 0.002 | 0.000 |
| 720 | 0.003 | 0.001 | 0.000 |
| 725 | 0.002 | 0.001 | 0.000 |
| 730 | 0.001 | 0.001 | 0.000 |
| 735 | 0.001 | 0.000 | 0.000 |
| 740 | 0.001 | 0.000 | 0.000 |
| 745 | 0.001 | 0.000 | 0.000 |
| 750 | 0.000 | 0.000 | 0.000 |
| 755 | 0.000 | 0.000 | 0.000 |
| 760 | 0.000 | 0.000 | 0.000 |
| 765 | 0.000 | 0.000 | 0.000 |
| 770 | 0.000 | 0.000 | 0.000 |
| 775 | 0.000 | 0.000 | 0.000 |
| 780 | 0.000 | 0.000 | 0.000 |

List of Reference Symbols

| | |
|---|---|
| 1, 2, 3 | Broad band light source |
| 4 | Beam splitter |
| 5 | Reference mirror |
| 6 | Sample object |
| 7 | Photo sensor |
| 10 | Tunable light source |
| 11 | Multi-mode optical fiber |
| 12 | Beam splitter |
| 13 | Reference mirror |
| 14 | Sample object |
| 15 | Photo sensor |
| 20 | Tunable light source |
| 21 | Multi-mode optical fiber |
| 22 | Collimating lens |

-continued

List of Reference Symbols

| | |
|---|---|
| 23 | Beam splitter |
| 24 | Deflection mirror |
| 25 | Optical subsystem module |
| 26 | Reference mirror |
| 27 | Reference imaging lens |
| 28 | Compensation plate |
| 29 | Neutral density plate |
| 30 | Object plane |
| 31 | Object imaging lens |
| 32 | Optical aperture |
| 33 | Detector imaging lens |
| 34 | Photo sensor |
| 40, 41, 42 | Absorbing layer |
| 43 | Reference object |

The invention claimed is:

1. A colorimetric optical coherence tomography microscopy apparatus for recording three-dimensional images of optically translucent or reflective sample objects, comprising a broadband light source, and an interferometric optical setup for detecting a three-dimensional image of an optically translucent or reflective object, wherein said broadband light source is a tunable light source that is able to produce light over the complete visual spectrum according to the CIE tristimulus curves and wherein said interferometric optical setup provides a dynamic coherence focus with respect to the reference beam path and the object beam path over the full scanning distance when recording three-dimensional images, wherein dispersion effects caused by different effective propagation velocities of different illumination light spectra are corrected by said apparatus by:

carrying out a multitude of depths scans with illumination light having different spectra;

identifying salient features in the different depth scans originating from the same optical structures in the object; and adjusting the depth scan axes of the different depth scans so that the corresponding salient features in the different depth scans coincide.

2. The microscopy apparatus according to claim 1, wherein the emitted spectra are such that an effective spectral distribution of the light detected by said interferometric optical setup is proportional to the CIE tristimulus curves $\bar{x}$, $\bar{y}$ and $\bar{z}$ or a linear combination thereof, if an object with spectrally constant, white reflectance is employed as the sample object.

3. The microscopy apparatus according to claim 2, wherein the interferometric optical setup for detecting three-dimensional images of an optically translucent or reflective object comprises a beam splitter, arranged to split up a collimated beam of light produced by the broadband light source into a reference beam and an object beam, and arranged to recombine the reference beam and the object beam to a detection beam; a movable, planar reference mirror, arranged to reflect said reference beam back to the beam splitter; a movable object imaging lens; arranged to focus said object beam to an object focus plane, and to collimate light reflected from said object focus plane back to the object light beam; actuator means for synchronously moving the reference mirror and the object imaging lens; a photo sensor, able to convert incident light to an electric current signal; and a detector imaging lens, arranged to focus the detection beam coming from the beam splitter to the photo sensor; the apparatus comprises one or more planar deflection mirrors that are arranged to deflect the reference beam and/or the object beam exiting the beam splitter in such a way that the reference beam and the object beam are oriented parallel to each other; and a movable reference imaging lens, arranged to focus the reference beam coming from the beam splitter to the plane of the reference mirror; wherein the reference mirror, the reference imaging lens, and the object imaging lens have fixed positions to each other, and are arranged to be moved as a unit by the actuator means; the photo sensor is a two-dimensional image sensor with a plurality of pixel elements;

the pixel elements of the two-dimensional image sensor are able to individually demodulate the detected signal; the reference imaging lens, and the object imaging lens have identical optical properties and geometric dimensions; one or more compensation plates are placed in the reference beam and/or the object beam, in a fixed position in relation to the reference mirror, the reference imaging lens, and the object imaging lens, wherein the one and more compensation plates correct for differences in the optical properties and geometric dimensions of the reference imaging lens, and the object imaging lens, so that the total effective thickness and the refractive properties of the materials in both the reference beam path and the object beam path are identical; one of the reference mirror, the reference imaging lens, and the object imaging lens are arranged in an exchangeable cartridge, and a compensation plate is placed in the object beam, in a fixed position in relation to the object imaging lens, and that the compensation plate and the object imaging lens are arranged in an exchangeable cartridge; the tunable light source is a tunable monochromatic light source with electronically changeable and controllable frequency.

4. The microscopy apparatus of claim 3, wherein absorption effects in a sample volume caused by homogeneous layers oriented perpendicular to the depth scan axis with unknown absorption characteristics are corrected by:

arranging one or more reference objects with known spectral reflectance characteristics in different depths in the sample volume;

obtaining the effective total attenuation coefficients of the distinct object planes, in which the reference objects are situated, by dividing a detector signal corresponding to the light reflected by one single reference object by the product of the optical reflectance ratio of said single reference object and the emitted light power; and applying the obtained effective attenuation coefficients for correcting a three-dimensional color image of the sample object; and wherein separate effective total attenuation coefficients are obtained for different applied illumination light spectra.

5. The microscopy apparatus according to claim 1, wherein the interferometric optical setup for detecting three-dimensional images of an optically translucent or reflective object comprises a beam splitter, arranged to split up a collimated beam of light produced by the broadband light source into a reference beam and an object beam, and which is arranged to recombine the reference beam and the object beam to a detection beam;

a movable, planar reference mirror, arranged to reflect said reference beam back to the beam splitter;

a movable object imaging lens arranged to focus said object beam to an object focus plane, and to collimate light reflected from said object focus plane back to the object light beam;

an opto-mechanical scanner enabling the synchronous moving of the reference mirror and the object imaging lens;

a photo sensor, able to convert incident light to an electric current signal; and a detector imaging lens, arranged to focus the detection beam coming from the beam splitter to the photo sensor.

6. The microscopy apparatus according to claim 5, wherein the apparatus comprises:

one or more planar deflection mirrors that are arranged to deflect the reference beam and/or the object beam exiting the beam splitter in such a way that the reference beam and the object beam are oriented parallel to each other; and a movable reference imaging lens, arranged to focus the reference beam coming from the beam splitter to the plane of the reference mirror;

wherein the reference mirror, the reference imaging lens, and the object imaging lens have fixed positions to each other, and are arranged to be moved as a unit by the opto-mechanical scanner.

7. The microscopy apparatus according to claim 5, wherein the photo sensor is a two-dimensional image sensor with a plurality of pixel elements.

8. The microscopy apparatus according to claim 7, wherein the pixel elements of the two-dimensional image sensor are able to individually demodulate the detected signal.

9. The microscopy apparatus according to claim 5, wherein the reference imaging lens, and the object imaging lens have identical optical properties and geometric dimensions.

10. The microscopy apparatus according to claim 5, wherein at least one compensation plate is placed in the reference beam and/or the object beam, in a fixed position in relation to the reference mirror, the reference imaging lens, and the object imaging lens, wherein the at least one compensation plate corrects for differences in the optical properties and geometric dimensions of the reference imaging lens, and the object imaging lens, so that the total effective thickness and the refractive properties of the materials in both the reference beam path and the object beam path are identical.

11. The microscopy apparatus according to claim 5, wherein the reference mirror, the reference imaging lens, and the object imaging lens are arranged in an exchangeable cartridge.

12. The microscopy apparatus according to claim 5, wherein the at least one compensation plate is placed in the object beams in a fixed position in relation to the object imaging lens, and wherein the at least one compensation plate and the object imaging lens are arranged in an exchangeable cartridge.

13. The microscopy apparatus according to claim 1, wherein the tunable light source is a tunable monochromatic light source with electronically changeable and controllable frequency.

14. The microscopy apparatus according to claim 1, wherein the apparatus is a time encoded frequency domain OCT apparatus, and the relative displacement of the optical signals from the reference beam path and the object beam path is realized using a tunable monochromatic light source, whose frequency can be changed and controlled electronically.

15. The microscopy apparatus of claim 14, wherein three depth scans are carried out.

16. The apparatus according to claim 14, wherein absorption effects in a sample volume caused by homogeneous layers oriented perpendicular to the depth scan axis with unknown absorption characteristics are corrected by:

arranging one or more reference objects with known spectral reflectance characteristics in different depths in the sample volume;

obtaining the effective total attenuation coefficients of the distinct object planes, in which the reference objects are situated, by dividing a detector signal corresponding to the light reflected by one single reference object by the product of the optical reflectance ratio of said single reference object and the emitted light power; and applying the obtained effective attenuation coefficients for correcting a three-dimensional color image of the sample object; and wherein separate effective total attenuation coefficients are obtained for different applied illumination light spectra.

17. The apparatus according to claim 1, wherein three depth scans are carried out by said apparatus.

18. The apparatus according to claim 1 wherein absorption effects in a sample volume caused by homogeneous layers oriented perpendicular to the depth scan axis with unknown absorption characteristics are corrected by arranging one or more reference objects with known spectral reflectance characteristics in different depths in the sample volume;

obtaining the effective total attenuation coefficients of the distinct object planes, in which the reference objects are situated, by dividing a detector signal corresponding to the light reflected by one single reference object by the product of the optical reflectance ratio of said single reference object and the emitted light power; and applying the obtained effective attenuation coefficients for correcting a three-dimensional color image of the sample object.

19. The microscopy apparatus according to claim 18, wherein separate effective total attenuation coefficients are obtained for different applied illumination light spectra.

20. The microscopy apparatus of claim 1, wherein three depth scans are carried out.

21. A colorimetric optical coherence tomography microscopy apparatus for recording three-dimensional images of optically translucent or reflective sample objects, comprising a broadband light source, and an interferometric optical setup for detecting a three-dimensional image of an optically translucent or reflective object, wherein said broadband light source is a tunable light source that is able to produce light over the complete visual spectrum according to the CIE tristimulus curves and wherein said interferometric optical setup provides a dynamic coherence focus with respect to the reference beam path and the object beam path over the full scanning distance when recording three-dimensional images, wherein absorption effects caused by homogeneous layers oriented perpendicular to the depth scan axis with unknown absorption characteristics are corrected by said apparatus by:

arranging one or more reference objects with known spectral reflectance characteristics in different depths in the sample volume;

obtaining the effective total attenuation coefficients of the distinct object planes, in which the reference objects are situated, by dividing a detector signal corresponding to the light reflected by one single reference object by the product of the optical reflectance ratio of said single reference object and the emitted light power; and applying the obtained effective attenuation coefficients for correcting a three-dimensional color image of the sample object.

22. The microscopy apparatus according to claim 21, wherein separate effective total attenuation coefficients are obtained for different applied illumination light spectra.

* * * * *

UNITED STATES PATENT AND TRADEMARK OFFICE
CERTIFICATE OF CORRECTION

| | |
|---|---|
| PATENT NO. | : 7,659,991 B2 |
| APPLICATION NO. | : 11/894960 |
| DATED | : February 9, 2010 |
| INVENTOR(S) | : Peter Seitz |

It is certified that error appears in the above-identified patent and that said Letters Patent is hereby corrected as shown below:

Column 1, line 9, "calorimetric" should be --colorimetric--;

Column 3, line 17, "calorimetric" should be --colorimetric--; and

Column 3, line 53, "d'Eclairage" should be --l'Eclairage--.

Signed and Sealed this
Eighth Day of February, 2011

David J. Kappos
*Director of the United States Patent and Trademark Office*